United States Patent
Taniguchi

(10) Patent No.: US 10,239,056 B2
(45) Date of Patent: Mar. 26, 2019

(54) MICRO FLOW CHANNEL CHIP AND METHOD FOR PRODUCING MICRO FLOW CHANNEL CHIP

(71) Applicant: SUMITOMO BAKELITE CO., LTD., Tokyo (JP)

(72) Inventor: Hirohito Taniguchi, Kobe (JP)

(73) Assignee: SUMITOMO BAKELITE COMPANY LIMITED, Tokyo (JP)

( * ) Notice: Subject to any disclaimer, the term of this patent is extended or adjusted under 35 U.S.C. 154(b) by 0 days.

(21) Appl. No.: 15/357,529

(22) Filed: Nov. 21, 2016

(65) Prior Publication Data

US 2017/0144151 A1     May 25, 2017

(30) Foreign Application Priority Data

Nov. 24, 2015   (JP) .................. 2015-228953

(51) Int. Cl.
*B01L 3/00*     (2006.01)
*G01N 33/543*     (2006.01)
(Continued)

(52) U.S. Cl.
CPC ... *B01L 3/502707* (2013.01); *B01L 3/502715* (2013.01); *B29C 65/02* (2013.01);
(Continued)

(58) Field of Classification Search
CPC .............................................. B01L 3/502707
(Continued)

(56) References Cited

U.S. PATENT DOCUMENTS 5,300,573 A * 4/1994 Patel .................. C08L 23/08
525/109
5,491,194 A * 2/1996 Henton .............. C08G 18/3212
525/66
(Continued)

FOREIGN PATENT DOCUMENTS

JP     2004-163269 A     6/2004

*Primary Examiner* — Christopher Adam Hixson
*Assistant Examiner* — Emily R. Berkeley
(74) *Attorney, Agent, or Firm* — Westerman, Hattori, Daniels & Adrian, LLP

(57) ABSTRACT

A micro flow channel chip having high shape accuracy is provided. A micro flow channel chip includes a base material 12 having a groove 121 formed on one surface; and a resin film 14 joined to the surface of the base material 12 so as to cover the groove 121 of the base material 12, in which the resin film 14 contains a (meth)acrylic resin (A), and the (meth)acrylic resin (A) contains a structural unit (A1) represented by Formula (1).

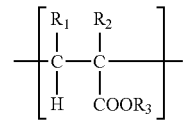

Formula (1)

(In Formula (1), $R_1$ and $R_2$ each independently represent a hydrogen atom, a methyl group, an ethyl group, or a propyl group; and $R_3$ represents an alkyl group having 3 to 6 carbon atoms).

7 Claims, 1 Drawing Sheet

(51) Int. Cl.
*B29C 65/00* (2006.01)
*B29C 65/02* (2006.01)
*B81C 3/00* (2006.01)
*B29L 31/00* (2006.01)

(52) U.S. Cl.
CPC .... *B29C 66/1122* (2013.01); *B29C 66/53461* (2013.01); *B29C 66/71* (2013.01); *B81C 3/001* (2013.01); *G01N 33/54366* (2013.01); *B01L 2300/0887* (2013.01); *B01L 2300/161* (2013.01); *B29C 66/026* (2013.01); *B29C 66/028* (2013.01); *B29L 2031/756* (2013.01)

(58) Field of Classification Search
USPC .......................................................... 422/503
See application file for complete search history.

(56) References Cited

U.S. PATENT DOCUMENTS

| | | | | |
|---|---|---|---|---|
| 2008/0057274 A1* | 3/2008 | Hagiwara | ......... | B01L 3/502738 428/172 |
| 2010/0323141 A1* | 12/2010 | Kawasaki | ............. | C08F 220/18 428/36.9 |
| 2015/0086446 A1* | 3/2015 | Saito | ................. | B01L 3/502707 422/503 |

* cited by examiner

[Fig. 1]
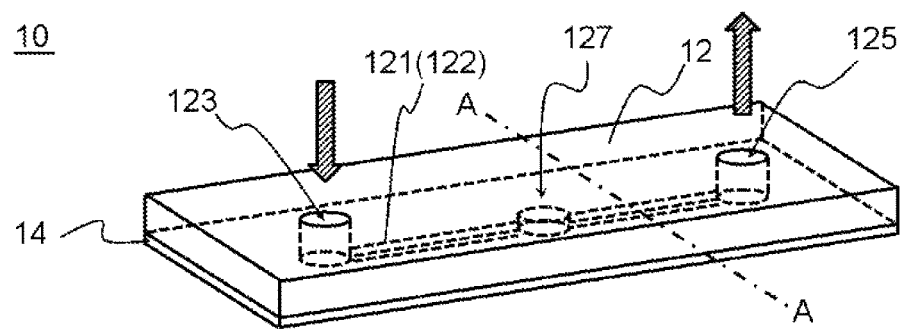
[Fig. 2(A)]
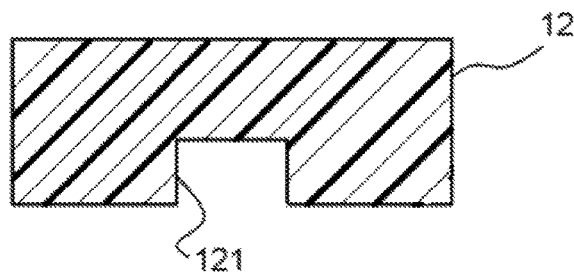
[Fig. 2(B)]
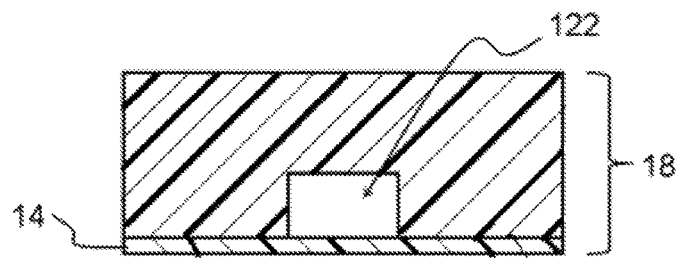

MICRO FLOW CHANNEL CHIP AND METHOD FOR PRODUCING MICRO FLOW CHANNEL CHIP

TECHNICAL FIELD OF THE INVENTION

The present invention relates to a micro flow channel chip and a method for producing a micro flow channel chip.

RELATED ART

In recent years, development of micro flow channel chips has been considered increasingly important.

Regarding the method for producing a micro flow channel chip, for example, as described in Patent Document 1, there is available a method for producing a micro flow channel chip by joining a substrate on which grooves for flow channels have been formed, with a cover member that covers the grooves.

PRIOR ART DOCUMENT

Patent Document

[Patent Document 1] Japanese Unexamined Patent Application, First Publication No. 2004-163269

DISCLOSURE OF THE INVENTION

Problems to be Solved by the Invention

While there is a demand for further size reduction and increased precision of micro flow channels, a substrate and a film as a member for covering the substrate are both required to have satisfactory formability.

However, with the method of Patent Document 1, it is difficult to cope with the demand for further size reduction and increased precision of the flow channel structure.

It is an object of the present invention to provide a micro flow channel chip having high shape accuracy, and a method for producing the same.

Means for Solving the Problem

In order to solve the problems described above, the present invention provides the following micro flow channel chip and a method for producing the same.

A micro flow channel chip including:
a base material having a groove formed on one surface; and
a resin film joined to the surface so as to cover the groove of the base material,
in which the resin film contains a (meth)acrylic resin (A), and
the (meth)acrylic resin (A) contains a structural unit (A1) represented by Formula (1).

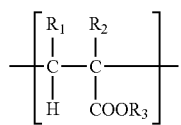

Formula (1)

(In Formula (1), $R_1$ and $R_2$ each independently represent a hydrogen atom, a methyl group, an ethyl group, or a propyl group; and $R_3$ represents an alkyl group having 3 to 6 carbon atoms)

A method for producing a micro flow channel chip, the method including:
a step of forming a groove on one surface of a base material; and
a step of joining a resin film to the surface so as to cover the groove of the base material,
in which the resin film contains a (meth)acrylic resin (A), and
the (meth)acrylic resin (A) contains a structural unit (A1) represented by Formula (1).

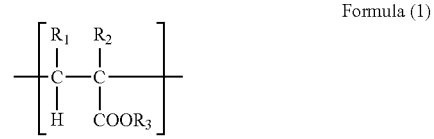

Formula (1)

(In Formula (1), $R_1$ and $R_2$ each independently represent a hydrogen atom, a methyl group, an ethyl group, or a propyl group; and $R_3$ represents an alkyl group having 3 to 6 carbon atoms)

Effects of the Invention

According to the invention, a micro flow channel chip having high shape accuracy can be provided.

BRIEF DESCRIPTION OF THE DRAWINGS

FIG. 1 is a perspective view illustrating an example the structure of a micro flow channel chip according to an embodiment.

FIG. 2 is a view for explaining a method for producing a micro flow channel chip according to the embodiment.

EMBODIMENTS OF THE INVENTION

Hereinafter, an embodiment of the invention will be described using the drawings. In all of the drawings, the same constituent elements will be assigned with the same reference numeral, and explanations will not be repeated as appropriate.

FIG. 1 is a perspective view illustrating a micro flow channel chip 10 according to the present embodiment. The micro flow channel chip 10 is used for a treatment or an analysis of a liquid sample. The micro flow channel chip 10 includes a base material 12 having a groove 121 formed on one surface, and a resin film 14 joined to the surface of the base material 12 so as to cover the groove 121 of the base material 12. The resin film 14 contains a (meth)acrylic resin (A), and the (meth)acrylic resin (A) contains a structural unit (A1) represented by Formula (1). The details will be explained below.

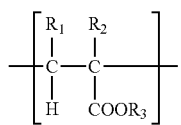

Formula (1)

(In Formula (1), $R_1$ and $R_2$ each independently represent a hydrogen atom, a methyl group, an ethyl group or a propyl group; and $R_3$ represents an alkyl group having 3 to 6 carbon atoms)

A micro flow channel chip 10 is used for a treatment or an analysis of a liquid sample. Here, the liquid sample is not particularly limited as long as it is a liquid; however, examples thereof include sweat, blood, a percolate, an interstitial fluid, urine, a tissue extract, and a liquid reagent.

Examples of the treatment of a liquid sample include detection or quantification of a specific substance in a liquid sample, and separation or mixing of a liquid sample.

The micro flow channel chip 10 is a micro flow channel chip on which, for example, structures such as fine flow channels, a reactive layer, an electric induction column, and a membrane separation mechanism have been formed. Specific examples of the micro flow channel chip 10 include fine reaction devices (microreactors) that are widely utilized in chemistry, biochemistry and the like; microanalysis devices such as an integrated type DNA analysis device, a microelectrophoresis device, and a microchromatography device; microdevices for preparing analytic samples for mass spectroscopy, liquid chromatography and the like; and physicochemical treatment devices for extraction, membrane separation, dialysis and the like.

Advantages of using such a chip include: (1) the amount of use and the amount of exhaust of the sample or reagent used for a chemical reaction or an antigen-antibody reaction can be reduced; (2) the electric power required for the process can be reduced; (3) as the ratio of the surface area to the volume is increased, an increase in the speed of thermal transfer and mass transfer can be realized, and as a result, precise control of the reaction or separation, speed and efficiency enhancement, and suppression of side reactions can be achieved; (4) many samples can be simultaneously handled on the same substrate; (5) processes including from sampling to detection can be conducted on the same substrate; and (6) an inexpensive system that is space-saving and portable can be realized. In order to further promote these advantages, it is requested to form a finer structure. On the other hand, since the flow or movement of a fluid strongly depends on the flow channel structure, it is becoming more important to form a desired fine structure with higher accuracy.

The micro flow channel chip 10 according to the present embodiment can realize satisfactory formability of the resin film 14, since the resin film 14 contains the above-described (meth)acrylic resin (A) that contains a structural unit (A1) represented by Formula (1). Therefore, in a case in which the base material 12 is joined with the resin film 14, the occurrence of lifting between the base material 12 and the resin film 14 can be suppressed. Furthermore, a micro flow channel chip which has high shape accuracy of flow channels, realizes a desired flow of a fluid, and has high reliability can be obtained. Meanwhile, the (meth)acrylic resin may be any one of an acrylic resin and a methacrylic resin.

The micro flow channel chip 10 illustrated in FIG. 1 includes an inlet port 123, an outlet port 125, and a detection unit 127. A liquid sample that is an object of examination is introduced through the inlet port 123, and flows through a flow channel 122 toward the outlet port 125. For example, in the detection unit 127 provided in the middle, a substance which reacts with a detection object substance (for example, a particular protein) and emits fluorescence is immobilized, so that whether the detection object substance is included in the liquid can be determined by observing the detection unit 127 with a fluorescence microscope or an optical detector. In this case, it is preferable that the micro flow channel chip 10 exhibits low autofluorescence. The configuration of the micro flow channel chip 10 is not limited to the configuration shown in FIG. 1, and various configurations can be adopted depending on the purpose.

Furthermore, the micro flow channel chip 10 may also be provided with a power mechanism or a control mechanism.

The detection method to be employed by the detection unit 127 is not limited to a method based on an optical principle, and may be a method based on a mechanical, electrical or chemical principle.

A groove 121 is provided on at least one principal surface of the base material 12, and may be provided on both of the principal surfaces of the base material 12. In regard to the micro flow channel chip 10 illustrated in FIG. 1, the flow channel 122 and the detection unit 127 are formed on one surface of the base material 12 as concavities having bottom surfaces. The inlet port 123 and the outlet port 125 are formed as through-holes in the base material 12.

The groove 121 is covered by the resin film 14. The groove 121 is a groove for a flow channel, and a tube-shaped structure formed as the opening of the groove 121 is covered by the resin film 14, is referred to as the flow channel 122. The resin film 14 may cover the entire opening of the groove 121, or may cover only a portion of the opening of the groove 121. In that case, a portion of the groove 121 may penetrate through an opening provided in the resin film 14 (not shown in the figure). The term "tube-shaped" is meant to include tube-shaped structures whose cross-section has any of a circular shape, an elliptical shape, a triangular shape, a rectangular shape, and a polygonal shape such as a pentagonal shape or a shape with a larger number of angles.

The micro flow channel chip 10 includes a flow channel 122 formed by a groove 121 having a width of, for example, 1 μm to 2 mm, preferably 5 μm to 1.8 mm, and more preferably 5 μm to 1.6 mm. Furthermore, the micro flow channel chip 10 includes a flow channel 122 formed by a groove 121 having a depth of, for example, 1 μm to 1 mm, preferably 5 μm to 800 μm, and more preferably 5 μm to 500 μm. The length of the flow channel 122 is, for example, 1 mm or more. When the width or depth is more than or equal to the lower limit described above, the micro flow channel chip 10 can be produced industrially efficiently. The micro flow channel chip 10 according to the present embodiment can realize a structure with high bonding accuracy, even if the flow channel 122 is fine, since the resin film 14 contains a (meth)acrylic resin (A). On the other hand, when the width or depth is smaller than or equal to the upper limit described above, remaining of air bubbles is suppressed, and it becomes easier to control the fluid that passes through the flow channel 122.

The thickness of the resin film 14 is preferably 50 μm or more, and more preferably 60 μm or more. The thickness of the resin film 14 is preferably 300 μm or less, and more preferably 200 μm or less. When the thickness is larger than or equal to the upper limit, and smaller than or equal to the lower limit, the base material 12 can be joined with high precision.

The resin film 14 can be produced using a resin composition for forming a resin film. The resin composition for forming a resin film includes a (meth)acrylic resin (A).

The (meth)acrylic resin (A) will be explained below. The (meth)acrylic resin (A) contains the structural unit (A1) represented by Formula (1).

Examples of the monomer that constitutes the (meth) acrylic resin (A) include acrylic acid, methacrylic acid, acrylic acid esters such as methyl acrylate, ethyl acrylate, butyl acrylate, and 2-ethylhexyl acrylate; methacrylic acid esters such as methyl methacrylate, ethyl methacrylate, and butyl methacrylate; acrylonitrile, methacrylonitrile, and acrylamide. The constituent monomer of the (meth)acrylic resin (A) includes one kind or two or more kinds of monomers among these examples. Furthermore, the constituent monomer of the (meth)acrylic resin (A) may further include monomers other than these examples.

The (meth)acrylic resin (A) is obtained by adding a polymerization initiator to a mixture of monomers, and then polymerizing the monomers. Examples of the polymerization initiator include organic peroxide-based polymerization initiators such as benzoyl peroxide, lauroyl peroxide, t-butyl peroxyisobutyrate, t-butyl peroxy-2-ethylhexanoate, t-butyl peroxyneodecanoate, t-hexyl peroxypivalate, diisopropyl peroxydicarbonate, and bis(4-t-butylcyclohexyl)peroxydicarbonate; and azo-based polymerization initiators such as 2,2'-azobisisobutyronitrile, 2,2'-azobis(2,4-dimethylvaleronitrile), and 2,2'-azobis(4-methoxy-2,4-dimethylvaleronitrile).

The (meth)acrylic resin (A) can be produced into a resin containing at least one structural unit between a structural unit derived from an acrylic acid alkyl ester having an alkyl group having 3 to 6 carbon atoms, and a structural unit derived from a methacrylic acid alkyl ester having an alkyl group having 3 to 6 carbon atoms.

From the viewpoint of enhancing formability of the resin film 14, it is preferable that the (meth)acrylic resin (A) contains a structure in which $R_3$ in Formula (1) is an alkyl group having 4 carbon atoms, as a structural unit (A1). That is, it is preferable that the (meth)acrylic resin (A) contains at least one structural unit between a structural unit derived from butyl acrylate and a structural unit derived from butyl methacrylate.

Whether the resin film 14 contains the (meth)acrylic resin (A), or whether the (meth)acrylic resin (A) contains a structure in which $R_3$ in Formula (1) is an alkyl group having 4 carbon atoms, as a structural unit (A1), can be determined by, for example, a mass analysis based on GC-MS (Gas Chromatography Mass Spectrometry).

In regard to the (meth)acrylic resin (A), the percentage content of the structural unit (A1) is preferably 0.5% or more. This percentage content is preferably 15% or less, more preferably 9% or less, and even more preferably 4% or less. When the percentage content is more than or equal to the lower limit, and less than or equal to the upper limit, formability can be further enhanced.

Here, the percentage content of the structural unit is the ratio of the mass of the relevant structural unit with respect to the total mass of the resin. The percentage content can be measured by, for example, a mass analysis based on GC-MS.

From the viewpoint of reducing flow channel deformation, it is preferable that the (meth)acrylic resin (A) further contains a structural unit (A2) represented by Formula (2), in addition to the structural unit (A1) represented by Formula (1). That is, it is preferable that the (meth)acrylic resin (A) further contains at least one structural unit between a structural unit derived from methyl acrylate and a structural unit derived from methyl methacrylate.

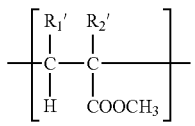

Formula (2)

(In Formula (2), $R_1'$ and $R_2'$ each independently represent a hydrogen atom, a methyl group, an ethyl group, or a propyl group)

Whether the (meth)acrylic resin (A) contains a structural unit (A2) can be determined by, for example, a mass analysis based on GC-MS.

The resin composition for forming a resin film may include two or more (meth)acrylic resins (A) having different structures, or may further include a (meth)acrylic resin that does not contain the structural unit (A1).

The resin composition for forming a resin film may further include one or more resins selected from the group consisting of resin materials such as polystyrene, polyethylene, polyvinyl chloride, polypropylene, polycarbonate, polyester, polyvinyl acetate, a vinyl-acetate copolymer, a styrene-methyl methacrylate copolymer, an acrylonitrile-styrene copolymer, an acrylonitrile-butadiene-styrene copolymer, nylon, polymethylpentene, a silicon resin, an amino resin, polysulfone, polyether sulfone, polyetherimide, a fluororesin, and polyimide.

The resin composition for forming a resin film may further include additives such as a pigment, a dye, an oxidation inhibitor, and a flame retardant.

The resin composition for forming a resin film is obtained by mixing the (meth)acrylic resin (A) with the other substances to be incorporated, as necessary.

The base material 12 can be produced using a resin composition for forming a base material. It is preferable that the resin composition for forming a base material includes a (meth)acrylic resin (B) that will be explained below.

The (meth)acrylic resin (B) is a resin containing a structural unit (B1) represented by Formula (3).

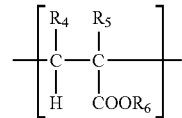

Formula (3)

(In Formula (3), $R_4$ and $R_5$ each independently represent a hydrogen atom, a methyl group, an ethyl group or a propyl group; and $R_6$ represents an alkyl group having 1 to 3 carbon atoms)

Whether the base material 12 contains a (meth)acrylic resin (B) containing a structural unit (B1) can be determined by, for example, a mass analysis based on GC-MS.

Examples of the monomer that constitutes the (meth)acrylic resin (B) include acrylic acid, methacrylic acid; acrylic acid esters such as methyl acrylate, ethyl acrylate, butyl acrylate, and 2-ethylhexyl acrylate; methacrylic acid esters such as methyl methacrylate, ethyl methacrylate, and butyl methacrylate; acrylonitrile, methacrylonitrile, and acrylamide. The constituent monomers of the (meth)acrylic resin (B) includes one kind or two or more kinds of monomers among these examples. Furthermore, the constituent monomers of the (meth)acrylic resin (B) may further include a monomer other than these examples.

The (meth)acrylic resin (B) is obtained by adding a polymerization initiator to a mixture of monomers, and then polymerizing the monomers. Examples of the polymerization initiator include organic peroxide-based polymerization initiators such as benzoyl peroxide, lauroyl peroxide, t-butyl peroxyisobutyrate, t-butyl peroxy-2-ethylhexanoate, t-butyl peroxyneodecanoate, t-hexyl peroxypivalate, diisopropyl peroxydicarbonate, and bis(4-t-butylcyclohexyl)peroxydicarbonate; and azo-based polymerization initiators such as 2,2'-azobisisobutyronitrile, 2,2'-azobis(2,4-dimethylvaleronitrile), and 2,2'-azobis(4-methoxy-2,4-dimethylvaleronitrile).

The (meth)acrylic resin (B) can be produced into a resin containing at least one structural unit between a structural unit derived from an acrylic acid alkyl ester having an alkyl group having 1 to 3 carbon atoms, and a structural unit derived from a methacrylic acid alkyl ester having an alkyl group having 1 to 3 carbon atoms.

From the viewpoint of enhancing formability, it is preferable that the (meth)acrylic resin (B) contains a structure in which $R_6$ in Formula (3) is an alkyl group having one carbon atom, as the structural unit (B1). That is, it is preferable that the (meth)acrylic resin (B) contains at least one structural unit between a structural unit derived from methyl acrylate and a structural unit derived from methyl methacrylate.

Whether the (meth)acrylic resin (B) contains a structure in which $R_6$ is an alkyl group having one carbon atom as the structural unit (B1), can be determined by, for example, a mass analysis based on GC-MS.

The resin composition for forming a base material may include two or more (meth)acrylic resins (B) having different components, or may further include a (meth)acrylic resin that does not contain the structural unit (B1).

The resin composition for forming a base material may further include one or more resins selected from the group consisting of resin materials such as polystyrene, polyethylene, polyvinyl chloride, polypropylene, polycarbonate, polyester, polyvinyl acetate, a vinyl-acetate copolymer, a styrene-methyl methacrylate copolymer an acrylonitrile-styrene copolymer, an acrylonitrile-butadiene-styrene copolymer, nylon, polymethylpentene, a silicon resin, an amino resin, polysulfone, polyether sulfone, polyetherimide, a fluororesin, and polyimide.

The resin composition for forming a base material may further include additives such as a pigment, a dye, an oxidation inhibitor, and a flame retardant.

The resin composition for forming a base material is obtained by mixing the (meth)acrylic resin (B) with the other substances to be incorporated, as necessary.

The base material 12 may be formed using a commercially available plate-shaped resin material. Also, the base material 12 can be produced from a material such as glass or silicon, in addition to a resin.

A method for producing the micro flow channel chip 10 will be explained using FIG. 2.

FIG. 2 is a view for explaining the method for producing a micro flow channel chip 10 according to the present embodiment. The micro flow channel chip 10 is used for a treatment or analysis of a liquid sample. This production method includes a step of forming a groove 121 on one surface of a base material 12; and a step of joining a resin film 14 to the surface of the base material 12 so as to cover the groove 121 of the base material 12.

First, in the step of forming a groove on the base material 12, as illustrated in FIG. 2(A), a base material 12 having a groove 121 formed on one surface thereof is prepared. The method for forming the groove 121 on the base material 12 is not particularly limited. For example, a groove 121 can be formed on a flat surface of a plate-shaped parent material formed from a resin composition for forming a base material, or a commercially available plate-shaped resin material, by machining, photolithography, laser abrasion, hot embossing, or the like, and thereby the base material 12 can be obtained. Alternatively, a resin composition for forming a base material can be used as a material, and a base material 12 having a groove 121 formed by a method such as injection molding using a predetermined mold. Here, the concavity that constitutes the detection unit 127, and the through-holes that constitute the inlet port 123 and the outlet port 125 are concurrently formed in the same manner.

Next, in the joining step, the resin film 14 is joined to the surface of the base material 12 so as to cover the groove 121 of the base material 12, and thereby a micro flow channel chip 10 such as illustrated in FIG. 2(B) is obtained. Specifically, the resin film 14 is prepared by forming the above-described resin composition for forming a resin film into a film form. Then, a laminate 18 obtained by disposing the resin film 14 on the surface of the base material 12, on which the groove 121 is provided, is subjected to pressure bonding. FIG. 2(B) is equivalent to a cross-sectional view cut along the line A-A in FIG. 1. According to the invention, in a case in which the resin film has an adhesive component or a pressure-sensitive adhesive component on the surface, the base material and the resin film can be joined by pressure bonding at normal temperature. Furthermore, in a case in which the resin film does not have the adhesive component or the pressure-sensitive adhesive component on the surface, the base material and the resin film can be joined by performing thermal pressure bonding.

After the step of forming a groove 121 on the base material 12 and before the step of joining, the base material 12 may be subjected to a surface treatment. In this case, the surface treatment is applied to the surface of the base material 12, on which the groove 121 has been formed. Examples of the surface treatment include a plasma treatment, a corona discharge treatment, and a surface coating treatment using a hydrophilic polymer. Examples of the hydrophilic polymer include polymers including polyethylene glycol (PEG), EVAL (EVOH). POVAL (PVOH), or a polymer having a phosphoylchloline group, as a component. When these surface treatments are performed, the inner wall of the flow channel 122 can be hydrophilized, and a satisfactory flow can be obtained.

Meanwhile, the flow channel (groove 121) of the micro flow channel chip 10 is appropriately designed by taking account of the object of detection and convenience.

The micro flow channel chip 10 may include a membrane, a valve, a sensor, a motor, a mixer, gears, a clutch, a microlens, an electrical circuit or the like, or may have a plurality of microchannel lines arranged side by side on the same substrate for compositization.

A biologically active substance may be immobilized in at least a portion of the flow channel of the micro flow channel chip 10. Examples of the biologically active substance include a nucleic acid, a protein, a sugar chain, and a glycoprotein. An optimal biologically active substance is selected as appropriate depending on the characteristics of the object of detection. Furthermore, a plurality of biologically active substances may be immobilized on the same channel, or different microchannels may be produced on the same micro flow channel device, and different biologically active substances may be immobilized in the respective microchannels. In order to immobilize a biologically active substance on the surface of a microchannel of a micro flow channel device, the plastic surface may be subjected to surface modification, for example, introduction of a functional group, immobilization of a functional material, impartation of hydrophilicity, and impartation of hydrophobicity.

The micro flow channel chip of the present embodiment having the above-described configuration has high shape accuracy. That is, an unintended flow or movement of a fluid in a fine flow channel, which is likely to be generated by deformation of the flow channel structure or the like, can be suppressed.

EXAMPLES

Hereinafter, the present embodiment will be described in detail by way of Examples. The embodiment is not intended to limit the description of these Examples by any means.

Example 1

A micro flow channel chip was produced according to the following procedure.

First, an acrylic substrate having a size of 50 mm×50 mm×1.5 mm in thickness was produced using an acrylic resin (manufactured by Sumitomo Chemical Co., Ltd., SUMIPEX LG2), and a flow channel groove having a width of 100 µm and a depth of 30 µm was formed using a cutting machine (manufactured by Roland DG Corporation, DESKTOP ENGRAVER EGX-350). Thus, this was used as a base material.

Meanwhile, as a resin film, a resin obtained by polymerizing 99.5 parts by weight of methyl methacrylate and 0.5 parts by weight of butyl acrylate was formed into a film form having a thickness of 125 µm, and thus an acrylic film 1 was obtained. Here, 2,2'-azobis(2,4-dimethylvaleronitrile) was used as a polymerization initiator. Since the yield with respect to the feed amount was almost 100%, the feed ratio of butyl acrylate can be regarded as the percentage content of the structural unit (A1) explained in connection with the embodiment.

Furthermore, it is understood that the resin contains a structural unit (A1) in which $R_3$ in Formula (1) is an alkyl group having 4 carbon atoms, and further contains a structural unit (A2) as explained in the embodiment. In the following description, the same also applies to Examples 2 to 7.

Next, the base material thus obtained and the resin film thus prepared were laminated, and the laminate was subjected to thermal pressure bonding using a heater. Thus, a micro flow channel chip was produced.

Examples 2 to 7

Micro flow channel chips were produced in the same manner as in Example 1, except that acrylic films 2 to 7 obtained by changing the feed ratio of butyl acrylate (percentage content of constituent unit (A1)) as shown in Table 1, were used instead of the acrylic film 1 as the resin film.

Comparative Example 1

A micro flow channel chip was produced in the same manner as in Example 1, except that an acrylic film 8 produced from a resin obtained by polymerizing only methyl methacrylate without incorporating butyl acrylate, was used instead of the acrylic film 1 as the resin film. The resin does not include a (meth)acrylic resin (A).

The micro flow channel chips produced in the various Examples and Comparative Example were subjected to the following evaluations.

(Presence or Absence of Inclusion of (meth)acrylic Resin (B))

It was investigated whether the base material contained the (meth)acrylic resin (B) containing a structural unit (B1) as explained in connection with the embodiment, by a mass analysis based on GC-MS.

As a result, it was confirmed that the base materials used in the various Examples and Comparative Examples contained the (meth)acrylic resin (B). Specifically, the (meth)acrylic resin (B) containing a structure in which $R_6$ in Formula (3) is an alkyl group having one carbon atom as the structural unit (B1), was included.

(Evaluation of Formability)

Formability was evaluated for the micro flow channel chips of the various Examples and Comparative Example. Specifically, the presence or absence of air bubble between the base material and the resin film was checked using a microscope.

Here, the "air bubble" represents a space between the base material and the resin film. The case in which lifting between the base material and the resin film was not observed was rated as "excellent"; the case in which lifting was slightly observed but there was no problem for use as a manufactured product was rated as "good"; and the case in which lifting was generally observed, and there was a problem for use as a manufactured product was rated as "worse". The results are presented in Table 1.

(Presence or Absence of Flow Channel Deformation)

The presence or absence of flow channel deformation was evaluated for the micro flow channel chips of the various Examples and Comparative Example. Specifically, the height of the flow channel was measured using a laser displacement meter manufactured by Keyence Corporation.

Thereby, it was checked whether there was any part in which the flow channel had been deformed because the resin film was embedded in the groove of the base material. The case in which deformation of the flow channel was not observed was rated as "excellent"; and the case in which deformation was observed in some part of the flow channel, but there was no problem for use as a manufactured product was rated as "good". The results are presented in Table 1.

(Adhesive Strength)

For the micro flow channel chips of the various Examples and Comparative Examples, the adhesive strength of the base material and the resin film was evaluated. Specifically, the resin film was manually peeled off from the base material, and the case in which cohesive detachment occurred was rated as "excellent"; and the case in which interfacial detachment occurred was rated as "worse". The results are presented in Table 1.

The evaluation results for the various Examples and Comparative Example are summarized in Table 1.

TABLE 1

| | | Example 1 | Example 2 | Example 3 | Example 4 | Example 5 | Example 6 | Example 7 | Comparative Example |
|---|---|---|---|---|---|---|---|---|---|
| Resin film | Presence or absence of inclusion of (meth)acrylic resin (A) | Present | Present | Present | Present | Present | Present | Present | Absent |
| | Percentage content (%) of constituent unit (A1) | 0.5 | 1.0 | 5.0 | 8.0 | 15.0 | 0.1 | 20.0 | — |

TABLE 1-continued

|  |  | Example 1 | Example 2 | Example 3 | Example 4 | Example 5 | Example 6 | Example 7 | Comparative Example |
|---|---|---|---|---|---|---|---|---|---|
| Base material | Presence or absence of inclusion of constituent unit (A2) | Present | Present | Present | Present | Present | Present | Present | Present |
|  | Presence or absence of inclusion of (meth)acrylic resin (B) | Present | Present | Present | Present | Present | Present | Present | Present |
|  | Evaluation of formability | Excellent | Excellent | Excellent | Excellent | Excellent | Good | Excellent | Worse |
| Presence or absence of flow channel deformation |  | Excellent | Excellent | Excellent | Excellent | Excellent | Excellent | Good | Excellent |
| Adhesive strength |  | Excellent | Excellent | Excellent | Excellent | Excellent | Excellent | Excellent | Excellent |

From the results described above, it was confirmed that the micro flow channel chips of Examples 1 to 7, in which the resin film contained a (meth)acrylic resin (A) containing a structural unit (A1), exhibited excellent formability. Therefore, it is understood that micro flow channel chips having high shape accuracy are obtained. On the other hand, the micro flow channel chip of Comparative Example 1 in which the resin film did not contain the (meth)acrylic resin (A), exhibited poor formability.

Hitherto, the embodiment of the invention have been described with reference to the drawings: however, these are intended only for illustrating the invention, and various configurations other than those described above may also be employed.

BRIEF DESCRIPTION OF THE REFERENCE SYMBOLS

10: MICRO FLOW CHANNEL CHIP
12: BASE MATERIAL
121: GROOVE
122: FLOW CHANNEL
123: INLET PORT
125: OUTLET PORT
127: DETECTION UNIT
14: RESIN FILM
18: LAMINATE

The invention claimed is:

1. A micro flow channel chip, comprising:
a base material having a groove formed on one surface; and
a resin film joined to the surface so as to cover the groove of the base material,
wherein the resin film contains a (meth)acrylic resin (A), and
the (meth)acrylic resin (A) contains a structural unit (A1) represented by Formula (1),

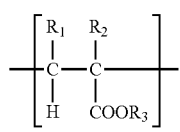

Formula (1)

wherein in Formula (1), $R_1$ and $R_2$ each independently represent a hydrogen atom, a methyl group, an ethyl group or a propyl group; and $R_3$ represents an alkyl group having 3 to 6 carbon atoms,
wherein the percentage content of all the structural unit (A1), including all combination of $R_1$, $R_2$ and $R_3$ groups, in all the (meth)acrylic resin (A) contained in the resin film is 0.5% to 15%.

2. The micro flow channel chip according to claim 1, wherein the (meth)acrylic resin (A) contains a structure in which $R_3$ in Formula (1) is an alkyl group having 4 carbon atoms, as the structural unit (A1).

3. The micro flow channel chip according to claim 1, wherein the (meth)acrylic resin (A) further contains a structural unit (A2) represented by Formula (2),

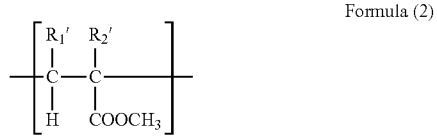

Formula (2)

wherein in Formula (2), $R_1'$ and $R_2'$ each independently represent a hydrogen atom, a methyl group, an ethyl group, or a propyl group.

4. The micro flow channel chip according to claim 1, wherein the base material contains a (meth)acrylic resin (B), and
the (meth)acrylic resin (B) contains a structural unit (B1) represented by Formula (3),

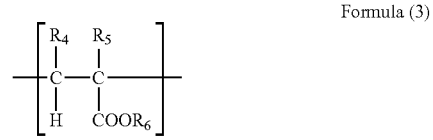

Formula (3)

wherein in Formula (3), $R_4$ and $R_5$ each independently represent a hydrogen atom, a methyl group, an ethyl group, or a propyl group; and $R_6$ represents an alkyl group having 1 to 3 carbon atoms.

5. The micro flow channel chip according to claim 4, wherein the (meth)acrylic resin (B) contains a structure in which $R_6$ in Formula (3) is an alkyl group having one carbon atom, as the structural unit (B1).

6. The micro flow channel chip according to claim 1, wherein the thickness of the resin film is from 50 μm to 300 μm.

7. The micro flow channel chip according to claim 1, wherein the depth of the groove is from 1 μm to 1 mm.

* * * * *